United States Patent
Kucklick

(10) Patent No.: US 9,833,134 B2
(45) Date of Patent: Dec. 5, 2017

(54) PROTECTIVE CAP FOR ARTHROSCOPIC INSTRUMENTS

(71) Applicant: Cannuflow, Inc., Campbell, CA (US)

(72) Inventor: Theodore R. Kucklick, Campbell, CA (US)

(73) Assignee: Cannuflow, Inc., Campbell, CA (US)

( * ) Notice: Subject to any disclaimer, the term of this patent is extended or adjusted under 35 U.S.C. 154(b) by 218 days.

(21) Appl. No.: 14/924,586

(22) Filed: Oct. 27, 2015

(65) Prior Publication Data

US 2016/0045105 A1 Feb. 18, 2016

Related U.S. Application Data

(63) Continuation of application No. 13/545,886, filed on Jul. 10, 2012, now Pat. No. 9,167,955, which is a continuation of application No. 12/491,566, filed on Jun. 25, 2009, now Pat. No. 8,216,131, which is a continuation of application No. 11/142,990, filed on Jun. 1, 2005, now Pat. No. 7,553,278.

(51) Int. Cl.
*A61B 1/00* (2006.01)
*A61B 1/015* (2006.01)
*A61B 1/317* (2006.01)
*A61B 1/012* (2006.01)

(52) U.S. Cl.
CPC .......... *A61B 1/317* (2013.01); *A61B 1/00135* (2013.01); *A61B 1/00137* (2013.01); *A61B 1/00142* (2013.01); *A61B 1/012* (2013.01); *A61B 1/00089* (2013.01); *A61B 1/00096* (2013.01); *A61B 1/00177* (2013.01); *A61B 1/00183* (2013.01)

(58) Field of Classification Search
CPC . A61B 1/317; A61B 1/00135; A61B 1/00137; A61B 1/00142; A61B 1/012; A61B 1/00089; A61B 1/00096; A61B 1/00101; A61B 1/00154
See application file for complete search history.

(56) References Cited

U.S. PATENT DOCUMENTS

| | | | | |
|---|---|---|---|---|
| 3,051,176 A | * | 8/1962 | Alberti | A61B 1/31 600/117 |
| 4,470,407 A | * | 9/1984 | Hussein | A61B 1/00082 600/108 |
| 4,809,678 A | * | 3/1989 | Klein | A61B 1/00142 600/121 |
| 4,809,679 A | * | 3/1989 | Shimonaka | A61B 1/00137 600/154 |
| 4,856,495 A | * | 8/1989 | Tohjoh | A61B 1/00096 600/175 |
| 4,867,546 A | * | 9/1989 | Nishioka | G02B 23/243 359/714 |
| 5,029,574 A | * | 7/1991 | Shimamura | A61B 1/00082 600/108 |

(Continued)

*Primary Examiner* — John P Leubecker
(74) *Attorney, Agent, or Firm* — K. David Crockett, Esq.; Susan L. Crockett, Esq.; Crockett & Crockett, PC

(57) ABSTRACT

A protective cap for use on arthroscopic instruments and sheaths disposed over arthroscopic instruments. The cap protects the distal end of the instrument from accidental damage caused by other instruments used during a surgical procedure. The cap has a flange disposed within an inner diameter of a bore within the cap to prevent the sheath from being pushed into the cap.

9 Claims, 6 Drawing Sheets

(56) References Cited

U.S. PATENT DOCUMENTS

| | | | | |
|---|---|---|---|---|
| 5,191,878 A | * | 3/1993 | Iida | A61B 1/00068 600/157 |
| 5,329,935 A | * | 7/1994 | Takahashi | A61B 1/00142 600/121 |
| 5,536,236 A | * | 7/1996 | Yabe | A61B 1/00089 600/121 |
| 5,695,448 A | * | 12/1997 | Kimura | A61B 1/0005 600/114 |
| 5,863,287 A | * | 1/1999 | Segawa | A61B 1/00142 600/121 |
| 6,010,450 A | * | 1/2000 | Perkins | A61B 1/00096 359/799 |
| 6,095,970 A | * | 8/2000 | Hidaka | A61B 1/00124 600/109 |
| 6,447,444 B1 | * | 9/2002 | Avni | A61B 1/0005 600/109 |
| 7,033,317 B2 | * | 4/2006 | Pruitt | A61B 1/00096 600/129 |
| 2002/0035311 A1 | * | 3/2002 | Ouchi | A61B 1/00089 600/175 |
| 2004/0143162 A1 | * | 7/2004 | Krattiger | A61B 1/00096 600/175 |
| 2004/0147807 A1 | * | 7/2004 | Viebach | A61B 1/0008 600/129 |
| 2005/0197530 A1 | * | 9/2005 | Wallace | A61B 1/00082 600/116 |
| 2006/0084839 A1 | * | 4/2006 | Mourlas | A61B 1/00082 600/116 |

\* cited by examiner

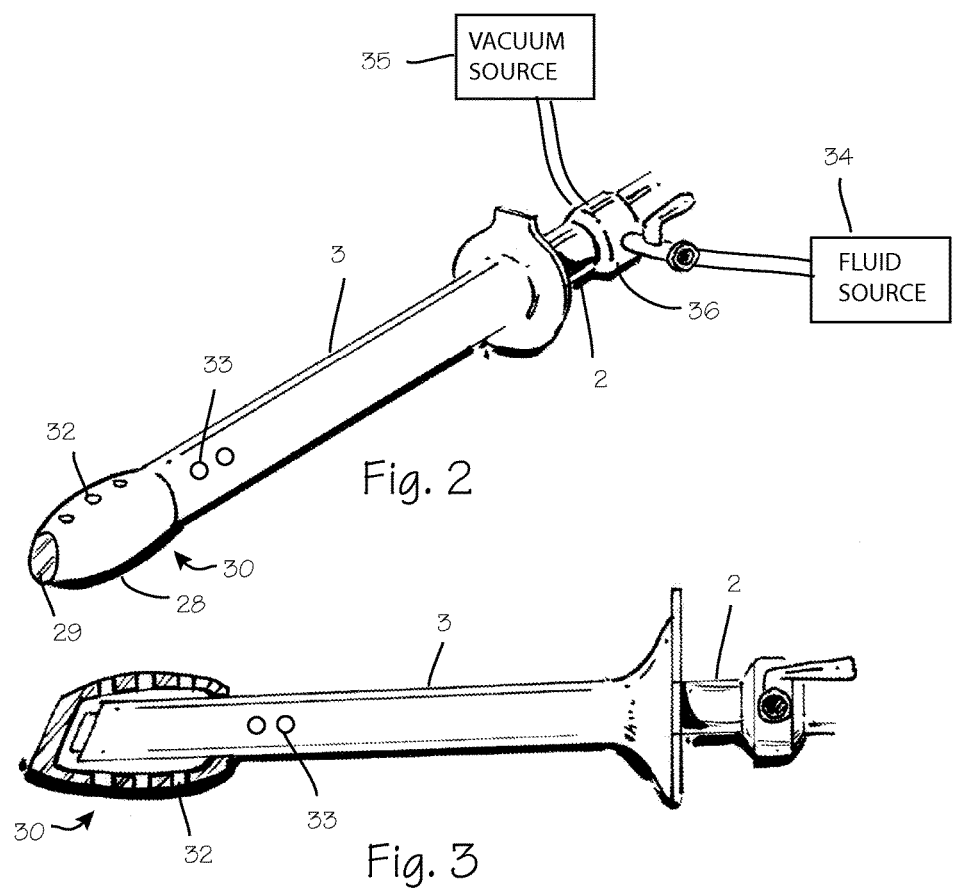

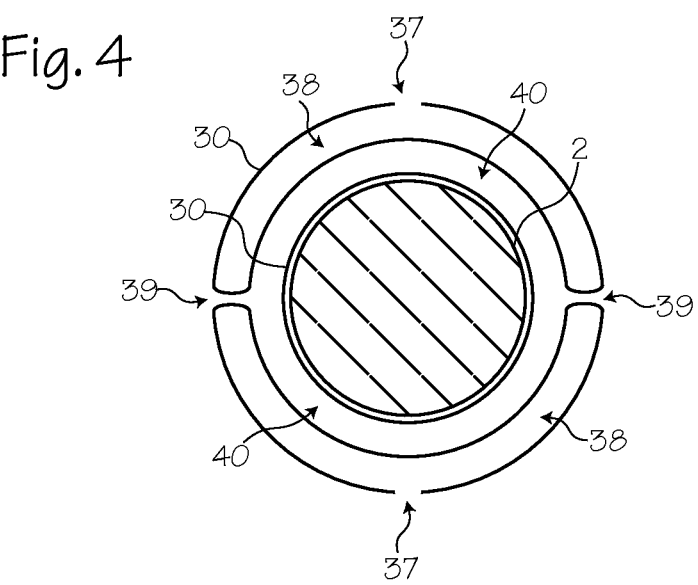

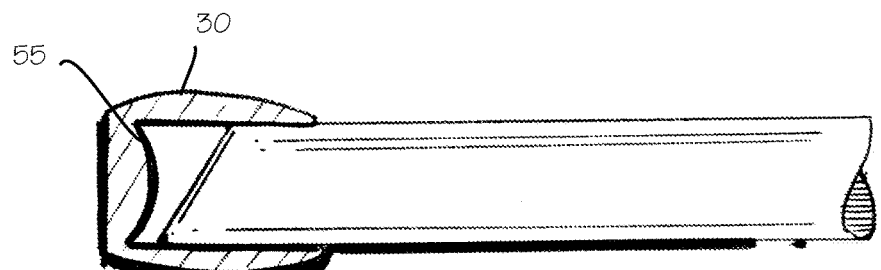
Fig. 5
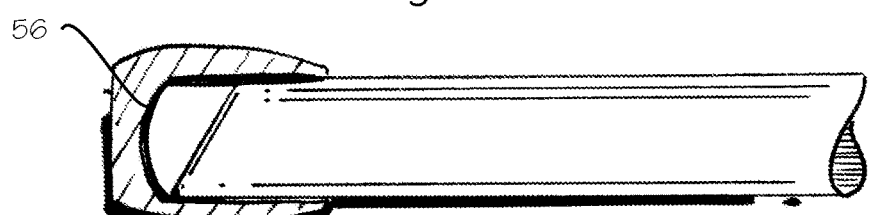
Fig. 6
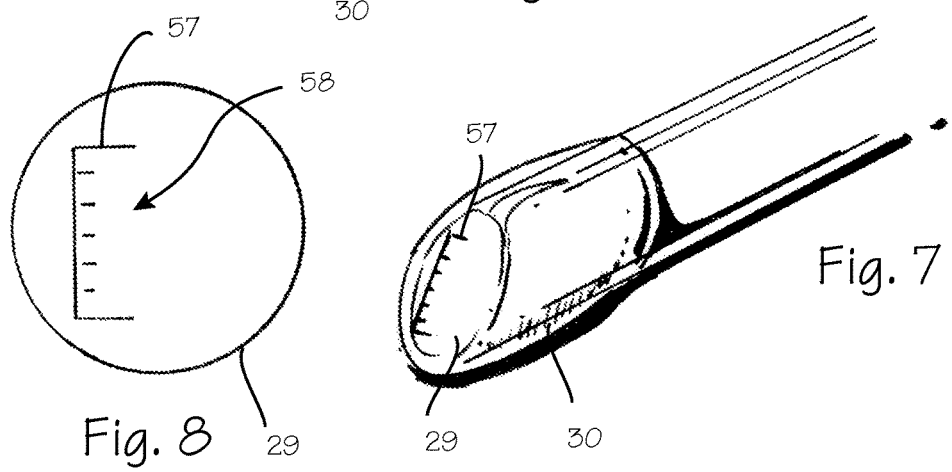
Fig. 8
Fig. 7

PROTECTIVE CAP FOR ARTHROSCOPIC INSTRUMENTS

This application is a continuation of U.S. patent application Ser. No. 13/545,886 filed Jul. 10, 2012, now U.S. Pat. No. 9,167,955, which is a continuation of U.S. patent application Ser. No. 12/491,566 filed Jun. 25, 2009, now U.S. Pat. No. 8,216,131, which is a continuation of Ser. No. 11/142,990, filed Jun. 1, 2005, now U.S. Pat. No. 7,553,278.

FIELD OF THE INVENTIONS

The inventions described below relate to the field of arthroscopic surgical instruments.

BACKGROUND OF THE INVENTIONS

Arthroscopic surgery involves using optical instruments, such as an arthroscope, to visualize an operating field inside or near a joint of a patient. The same instrument or other instruments may be used to perform a surgical procedure in the operating field. Common instruments used in addition to the arthroscope include a trimming instrument for cutting tissue and an irrigation instrument for irrigating the surgical field. Each of the instruments requires its own incision to be introduced into the surgical field; thus, many surgeons prefer to use only a trimming instrument and an arthroscope during arthroscopic surgical procedures.

Arthroscopes are fragile in relation to the forces applied during arthroscopic surgery, so a rigid cannula is placed over the arthroscope to reinforce it. The distal end of the rigid cannula is pointed, usually sharp, and so the rigid cannula can scratch or gouge soft tissue within the operating field. The rigid cannula can also become stuck between bones or cartilage during a procedure. A rigid cannula can also damage metal prosthetics used to replace joints, resulting in a shortening of the useful life of the prosthetic and forcing the patient to undergo additional, painful surgeries to correct the problem.

An additional problem associated with arthroscopic surgery is maintaining a clear surgical field during surgery. Blood and debris can cloud the field, impairing a surgeon's ability to visualize tissue. One method of solving this problem is to use the irrigation instrument to clear the surgical field with saline; however, many surgeons strongly prefer to avoid the additional trauma caused by inserting a third instrument. These surgeons will perform arthroscopic surgeries despite problems with visualizing the surgical field.

A further problem associated with arthroscopic surgery is accidental damage to the arthroscope. The arthroscope is often damaged if the working end of a trimming instrument accidentally strikes the sensitive optical components on the distal portion of the arthroscope. The arthroscope may also be damaged if the arthroscope becomes stuck between bones, cartilage or other tissue and excessive force must be used to free the arthroscope. Arthroscopes are expensive, costing thousands of dollars, so accidental damage to arthroscopes is a significant cost problem. A damaged arthroscope could cause delays during surgery and broken pieces of the arthroscope could be deposited in the surgical field. Both situations are harmful to the patient. Thus, devices and methods are needed to prevent accidental damage to arthroscopes during surgery.

SUMMARY

The methods and devices shown below provide for a protective cap that is placed over the distal portion of an arthroscope. The cap is made of a transparent, yet durable material that prevents accidental damage to the arthroscope caused by trimming instruments or impacts with hard tissue within the surgical field. Holes may be placed in the cap to provide for the inflow and outflow of fluids from the cap. One or more lenses or filters may be provided within the cap to adjust the field of view as seen through the arthroscope.

BRIEF DESCRIPTION OF THE DRAWINGS

FIG. 2 shows a protective cap disposed over the distal portion of an arthroscopic instrument.

FIG. 3 shows a cross section of a protective cap disposed over the distal portion of an arthroscopic instrument.

FIG. 4 shows a cross section of a multi-lumen protective cap.

FIG. 5 shows a protective cap having a concave lens disposed at the distal end of the cap.

FIG. 6 shows a protective cap having a convex lens disposed at the distal end of the cap.

FIG. 7 shows cap with a reticule for use with an arthroscopic instrument.

FIG. 8 shows a reticule for use with an arthroscopic instrument.

DETAILED DESCRIPTION OF THE INVENTIONS

Figure 1:
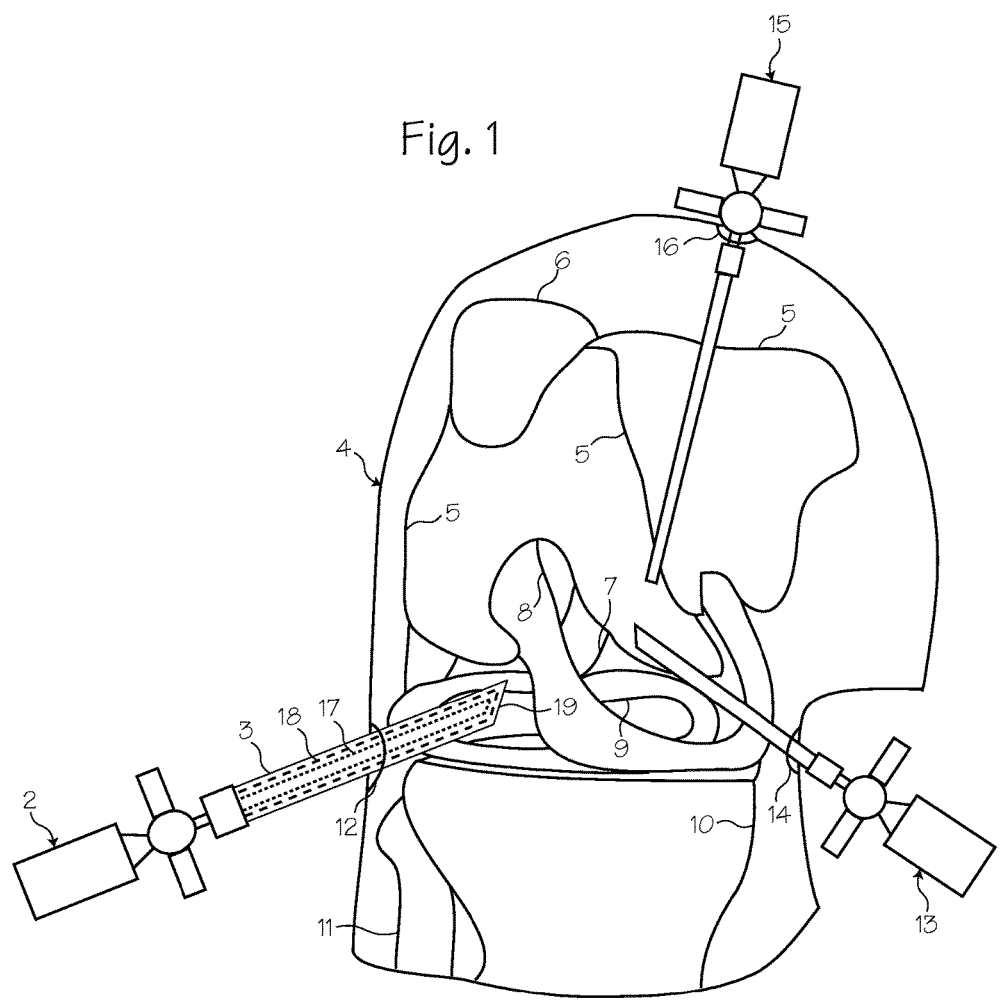
FIG. 1 shows a method of performing arthroscopic surgery on a patient.

FIG. 1 shows a method of performing arthroscopic surgery on a patient using an arthroscopic instrument 2 sheathed in an atraumatic introducer sheath 3. (The various parts of the arthroscope are shown in phantom to indicate their positions inside the sheath.) Various anatomical landmarks in a patient's knee 4 are shown for reference, including the femur 5, patella 6, posterior cruciate ligament 7, anterior cruciate ligament 8, meniscus 9, tibia 10 and fibula 11. During surgery, the surgeon introduces the arthroscope 2 into the knee via a first incision 12 in order to visualize the surgical field. A trimming instrument 13 is introduced through a second incision 14 to remove or trim tissue that the surgeon determines should be removed or trimmed. Optionally, an irrigating instrument 15 may be introduced through a third incision 16 in order to irrigate the surgical field and thereby maintain a clear view. As illustrated below, a combined arthroscope and inflow/outflow atraumatic sheath may replace the irrigating instrument.

The arthroscope 2 is an optical instrument 17 surrounded by a rigid cannula 18 having a distal edge that typically is cut at an angle. To protect the patient from unintended injury or trauma during the procedure, the arthroscope has been inserted into a resilient outer introducer sheath or atraumatic sheath 3 that extends over the rigid cannula. Preferably, the distal tip 19 of the atraumatic sheath extends distally just past the distal end of the arthroscope and rigid cannula to further protect the patient.

FIGS. 2 and 3 show an atraumatic protective cap 30 having a cap body 28 and a lens 29 and disposed over the distal portion 31 of an arthroscopic instrument. The cap body 28 is sized and dimensioned and of such a profile as to allow passage into restricted joint anatomy. Preferably, the cap is disposed on the end of the sheath 3 and slides over the distal end of the arthroscope as the sheath is pulled over the arthroscope as shown in FIG. 2. (The sheath is also shown in our co-pending application Ser. No. 10/769,629, filed Jan. 29, 2004, which is hereby incorporated by reference in its entirety.) The sheath can be a tube of polymeric material sized and dimensioned to slip fit over the outer surface of a cannula or endoscope. The sheath may further be provided with longitudinal ribs characterizing fluid flow lumens between the outer surface of the cannula and the inner surface of the sheath. The cap, however, may also be provided as a separate device from the sheath as illustrated in FIG. 3. The cap is preferably provided with a rounded, or bulbous, shape that reduces the chances of injuring tissue during the surgical procedure. The cap is optically transparent to wavelengths of light used during surgery, though only that portion of the cap covering the view port of the arthroscope need be transparent. (The view port is that portion of the arthroscope through which the surgeon visualizes the surgical field.) The material of the cap is sufficiently durable that the cap will prevent accidental damage to the arthroscope caused by unintended contact with the working end of a trimming instrument, by unintended contact with burrs or other hard tissue within the surgical field or because of excessive force applied to the arthroscope. Preferably, the body of the cap may be manufactured from thermoplastic elastomers. However, other materials used to manufacture the body of the cap may include styrenic block copolymers (SBCs), thermoplastic olefins (TPOs), thermoplastic vulcanisates (TPVs), thermoplastic polyurethane elastomers (TPUs), copolyesters (COPEs) and copolyamides (COPAs). Thermosets such as silicone, urethane or latex may also be used to manufacture the cap body. Sterilizable elastomers are typically used to make the body of the cap while optically clear polycarbonate materials comprise the viewing lens 29 in the cap 30. Other materials suitable for the viewing lens include molded acrylic, styrene, polyolefin or silicon. Alternatively, the body of the cap and lens can also be manufactured from the same optically clear material reducing manufacturing and assembly costs. Such suitable material includes optically clear silicone available from Wacker Silicones™ and having a hardness ranging from approximately 30 Shore A to approximately 40 Shore D.

One or more holes 32 may be placed in the cap to provide for suction, irrigation or the injection of therapeutic agents. Similar holes 33 may also be placed in the sheath. The holes are in fluid communication with one or more of the lumens disposed in the sheath or arthroscope or disposed between the sheath and arthroscope. A fluid source 34 in fluid communication with one or more lumens is provided to irrigate the surgical field or to inject therapeutic agents into the surgical field. A vacuum source 35 in fluid communication with one or more of the lumens provides suction. A manifold 36 disposed on the sheath or arthroscope distributes the flow of fluids within the sheath or arthroscope.

In use, the sheath and protective cap are pulled over the arthroscope. The surgeon then inserts the arthroscope into the surgical field and subsequently performs a surgical procedure on the patient. If, during the procedure, the working end of a trimming instrument accidentally strikes the cap, the cap will prevent damage to the arthroscope. Likewise, the cap will prevent damage to the arthroscope if the arthroscope strikes a burr or other hard piece of tissue. Preferably, the cap is releasably attached to the sheath so that the cap may be easily replaced if damaged by these events.

FIG. 4 shows a cross section of a multi-lumen protective cap 30 and an arthroscope 2 disposed within the cap. One or more holes 37 extend from the outer diameter of the cap to the outer lumen 38. In addition, one or more additional holes 39 extend from the outer diameter of the cap, through the outer lumen and to the inner lumen 40 of the cap. The holes 39 communicating with the inner lumen do not communicate with the outer lumen, thereby isolating the inner and outer lumens. Thus, suction may be provided through one lumen and simultaneous irrigation provided through the other lumen. Alternatively, the cap may be provided as part of a system providing fluid inflow and outflow to a surgical site where fluid inflow and outflow is accomplished by devices other than an arthroscope or arthroscope sheath.

The cap 30 or cap body 28 shown in FIGS. 2 through 4 may be integrally formed with a sheath 3, attached to a sheath 3, or fit over a sheath 3. The cap may also be provided without the sheath. The cap may be placed directly over the distal portion of the arthroscope without an atraumatic sheath. The cap can be held to the arthroscope by friction fit between the scope and the cap, by a shrink tube, by an adhesive, by detents or by any other suitable mechanism. Preferably, the cap is removably attached so that the cap may be easily replaced. As with the cap disposed on the sheath, holes 32 may be provided to provide for the inflow and outflow of fluids.

FIG. 5 shows a protective cap 30 having a concave lens 53 disposed at the distal end of the cap. The lens is provided just inside and proximal the distal end of the cap. The concave lens provides for a wide-angle view of the surgical field.

FIG. 6 shows a protective cap 30 having a convex lens 54 disposed at the distal end of the cap. The lens is provided just inside and proximal the distal end of the cap. The convex lens provides for a magnified view of an object within the surgical field.

FIG. 7 and FIG. 8 show a reticule 55 for use with an arthroscopic instrument. The reticule may be etched into a lens 29 disposed within the cap or may be otherwise suitably placed on the cap or even on arthroscope itself. The reticule is marked with a scale 56 with which the surgeon can measure the size of objects seen through the arthroscope. The surgeon may also use the reticule to align the arthroscope within the surgical field.

In addition to the lenses and reticule shown in FIGS. 5 through 8, filters may be provided within the cap to reduce light reflected into the arthroscope or to block certain wavelengths of light. The filtered lens may comprise a polarizing filter, a bandpass filter, a color filter, or an interference filter. These filters can be used in conjunction with specialized light sources (eg. Ultraviolet or Infrared) and video processing for therapeutic and diagnostic purposes. Thus, the cap may be part of a complete system to diagnose pathology using different wavelengths of light and/or colors of light and filtering the light. Further, the cap may also be provided as part of system that delivers photonic energy to a surgical site to control and visualize photodynamic therapy.

Figure 9:
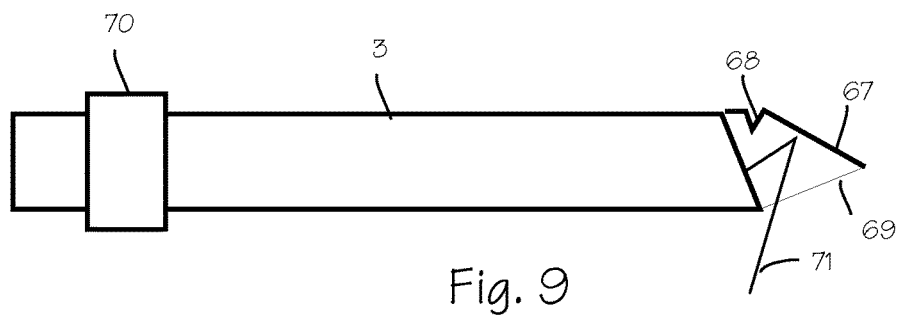
FIG. 9 illustrate an atraumatic sheath for use over an endoscope provided with a mirror having a hinge.
Figure 10:
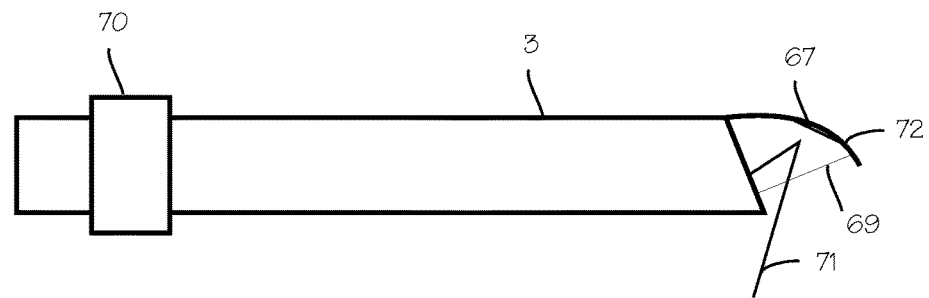
FIG. 10 illustrates an atraumatic sheath devices that allows viewing around an obstruction.

Other lenses, such as spherical lenses, may also be provided within the cap to change the field of view. Multiple lenses may also be provided within the cap to adjust the field of view. As illustrated in FIGS. 9 and 10, the sheath, the cap or the sheath with the cap combination may be configured to allow viewing around an object or obstruction. This may be accomplished through the use of a right angle prism, pentaprism, roof prism, retro-reflector or mirror disposed within the cap. The mirror may be flat, concave or convex to produce a normal, reduced, or magnified image. As illustrated in FIG. 9, an atraumatic sheath 3 for use over an endoscope is provided with a mirror 67 having a hinge 68. A pull-wire 69 is coupled to the mirror 67 and is disposed within the sheath 3. The pull-wire 69 is further coupled to an articulating knob 70. When the knob is manipulated, the pull-wire moves the mirror and changes the viewing angle 71.

FIG. 10 illustrates an atraumatic sheath 3 device that allows viewing around an object or obstruction through the use of a deflectable material or flexible mount 72 having a mirror 67. The mount may be manufactured from formable materials such as aluminum or steel having spring characteristics. A pull-wire 69 or other manipulation device may also be coupled to the mount to change viewing angle 71 when the wire is manipulated manually using an articulating knob 70. The mount may also be manufactured from shape memory materials such as Nitinol® that may be manipulated using electrical current to change the angle of the mirror. The cap and the sheath with the cap may also be modified for use with other types of endoscopes or for use with other delicate instruments that are subject to damage during a surgical procedure.

Figure 11:
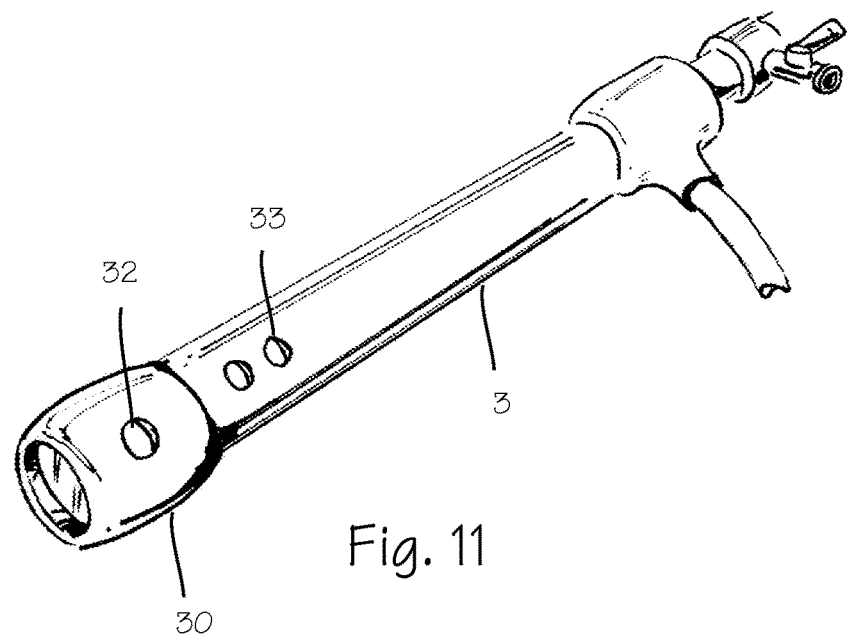
FIG. 11 shows a protective cap over an arthroscopic sheath.
Figure 12:
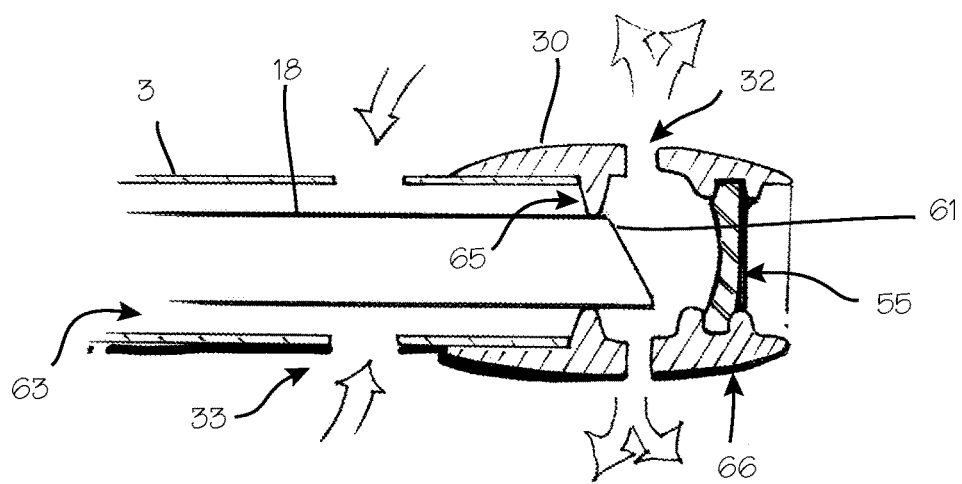
FIG. 12 shows a cross-section of protective cap over an arthroscopic sheath.

FIGS. 11 and 12 illustrate a protective cap 30 over an arthroscopic sheath 3. The sheath 3 comprises an inner lumen 63 in fluid communication with a vacuum source and a hole dispose 33 in the sheath in fluid communication with the vacuum source and a surgical site within a patient 1. A backstop or flange 65 is disposed within an inner diameter of a bore within the cap. The bore is sized and dimensioned to friction fit over the sheath 3.

The flange 65 prevents the sheath 3 from being further pushed into the cap and extends inwardly to come in contact with an outer diameter of the rigid cannula 18 disposed within the sheath 3. This contact forms a seal between the flange 65 and the outer diameter of the rigid cannula 18. The rigid cannula 18 is provided with a lumen in fluid communication with a fluid source the cap. Holes 32 disposed in the cap are in fluid communication with the surgical site and the lumen within the rigid cannula 18 as well as the fluid source allowing fluid to flow from the fluid source to the surgical site. The cap further comprises a concave lens 55 coupled to the distal portion 66 of the cap 3.

Thus, while the preferred embodiments of the devices and methods have been described in reference to the arthroscopic surgical environment in which they were developed, they are merely illustrative of the principles of the inventions. Other embodiments and configurations for use with other types of endoscopes may be devised for use in other surgical and non-surgical environments without departing from the spirit of the inventions and the scope of the appended claims.

I claim:

1. An atraumatic sheath in combination with an arthroscopic instrument disposed within a rigid cannula, said sheath comprising:
a tube characterized by a distal section and a proximal section wherein the inner diameter of said tube is sized and dimensioned to fit over an outer surface of the rigid cannula when the rigid cannula is disposed within the tube; and
a cap coupled to the distal end of the tube;
wherein said cap comprises a body bulbous in shape characterized by a distal end and proximal end, a bore having an inner diameter and disposed within the body, said inner diameter of said bore sized and dimensioned to friction fit over an outer diameter of the tube, a flange disposed within the inner diameter of the bore, the flange sized an dimensioned to friction fit over an outer diameter of the rigid cannula; and
a lens coupled to the distal end of the body and operably covering an objective lens of the arthroscopic instrument disposed within the rigid cannula.

2. The atraumatic sheath of claim 1 wherein the lens is concave.

3. The atraumatic sheath of claim 1 wherein the lens is convex.

4. A system for performing arthroscopic surgery, said system comprising:
an arthroscopic instrument suitable for performing an arthroscopic surgical procedure, said arthroscopic instrument characterized by a distal portion and a view port through which a surgical field may be visualized;
a rigid cannula, said rigid cannula characterized by a lumen and a distal tip, said rigid cannula sized and dimensioned such that the arthroscopic instrument may be extended through the lumen and distally of the distal tip of the rigid cannula;
a sheath characterized by a distal section and a proximal section wherein the inner diameter of said sheath is sized and dimensioned to fit over an outer surface of the rigid cannula when the rigid cannula is disposed within the sheath, a hole disposed in an outer surface of the sheath;
a cap disposed on the distal tip of the sheath, said cap having a portion covering the view port, wherein the portion of the cap covering the view port is transparent, wherein said cap comprises a body characterized by a distal end and proximal end, a bore having an inner diameter and disposed within the body, said inner diameter of said bore sized and dimensioned to friction fit over an outer diameter of the sheath, a flange disposed within the inner diameter of the bore, the flange sized an dimensioned to friction fit over an outer diameter of the rigid cannula; and
wherein a hole is disposed in an outer surface of the cap, said hole being in fluid communication with a lumen disposed in the rigid cannula.

5. The system of claim 4 wherein the lumen disposed in the rigid cannula is in fluid communication with a fluid source.

6. The system of claim 4 wherein a lumen disposed in the sheath is in fluid communication with a vacuum source.

7. The system of claim 6 further comprising a lens disposed on the portion of the cap covering the view port.

8. The system of claim 7 wherein the lens is a convex lens.

9. The system of claim 7 wherein the lens is a concave lens.

* * * * *